(12) United States Patent
Suddaby

(10) Patent No.: US 11,369,473 B2
(45) Date of Patent: Jun. 28, 2022

(54) EXTENDED RELEASE IMMUNOMODULATORY IMPLANT TO FACILITATE BONE MORPHOGENESIS

(71) Applicant: Loubert S. Suddaby, Orchard Park, NY (US)

(72) Inventor: Loubert S. Suddaby, Orchard Park, NY (US)

(*) Notice: Subject to any disclaimer, the term of this patent is extended or adjusted under 35 U.S.C. 154(b) by 87 days.

(21) Appl. No.: 16/377,314

(22) Filed: Apr. 8, 2019

(65) Prior Publication Data
US 2020/0315800 A1 Oct. 8, 2020

(51) Int. Cl.
| | | |
|---|---|---|
| *A61F 2/28* | (2006.01) | |
| *A61K 38/20* | (2006.01) | |
| *A61L 27/12* | (2006.01) | |
| *A61L 27/54* | (2006.01) | |
| *A61L 27/56* | (2006.01) | |
| *A61K 31/739* | (2006.01) | |
| *A61K 39/108* | (2006.01) | |
| *A61K 39/085* | (2006.01) | |

(Continued)

(52) U.S. Cl.
CPC ............ *A61F 2/28* (2013.01); *A61K 38/2026* (2013.01); *A61K 38/2066* (2013.01); *A61K 38/2086* (2013.01); *A61K 38/217* (2013.01); *A61K 39/0258* (2013.01); *A61K 39/085* (2013.01); *A61L 27/025* (2013.01); *A61L 27/06* (2013.01); *A61L 27/08* (2013.01); *A61L 27/12* (2013.01); *A61L 27/18* (2013.01); *A61L 27/3608* (2013.01); *A61L 27/54* (2013.01); *A61L 27/56* (2013.01); *A61F 2002/2817* (2013.01); *A61F 2002/2835* (2013.01); *A61F 2002/30006* (2013.01); *A61F 2002/30011* (2013.01); *A61F 2310/00023* (2013.01); *A61F 2310/00359* (2013.01); *A61K 31/739* (2013.01); *A61L 2300/252* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 5,409,703 A | 4/1995 | McAnalley et al. | |
| 5,755,792 A | 5/1998 | Brekke | |

(Continued)

FOREIGN PATENT DOCUMENTS

| | | |
|---|---|---|
| DE | 19811900 | 9/1999 |
| GB | 2370777 | 7/2002 |

(Continued)

OTHER PUBLICATIONS

Baht, Gurpreet S. et al. "The Role of the Immune Cells in Fracture Healing", Orthopedic Management of Fractures, Current Osteoporosis Reports (2018) 16:138-145, Springer, https://link.springer.com/article/10.1007/s11914-018-0423-2.

(Continued)

*Primary Examiner* — Leslie Lopez
(74) *Attorney, Agent, or Firm* — Michael Nicholas Vranjes; Harter Secrest & Emery LLP

(57) ABSTRACT

An extended release immunomodulatory implant operatively arranged to facilitate bone morphogenesis, including an inner portion including one or more interleukins, and an outer portion including an immunomodulatory stimulant such as an antigen.

19 Claims, 4 Drawing Sheets

(51) Int. Cl.

| | |
|---|---|
| *A61L 27/08* | (2006.01) |
| *A61L 27/02* | (2006.01) |
| *A61L 27/18* | (2006.01) |
| *A61L 27/06* | (2006.01) |
| *A61L 27/36* | (2006.01) |
| *A61K 38/21* | (2006.01) |
| *A61F 2/30* | (2006.01) |

(56) References Cited

U.S. PATENT DOCUMENTS

| | | | |
|---|---|---|---|
| 6,287,341 B1 | 9/2001 | Lee et al. | |
| 6,309,423 B2 | 10/2001 | Hayes | |
| 6,767,928 B1 | 7/2004 | Murphy et al. | |
| 7,371,425 B2 | 5/2008 | Rathenow et al. | |
| 7,709,018 B2 | 5/2010 | Pastorello et al. | |
| 7,923,436 B2 | 4/2011 | Monahan et al. | |
| 8,022,040 B2 | 9/2011 | Bertozzi et al. | |
| 8,124,687 B2 | 2/2012 | Wellisz et al. | |
| 8,512,741 B2 | 8/2013 | Tan et al. | |
| 8,518,431 B2 | 8/2013 | Spedden et al. | |
| 8,742,072 B2 | 6/2014 | Thorne | |
| 8,853,298 B2 | 10/2014 | Kasuga et al. | |
| 8,889,212 B2 | 11/2014 | O'Donoghue et al. | |
| 9,056,150 B2 | 6/2015 | Gross et al. | |
| 9,192,696 B2 | 11/2015 | Wang et al. | |
| 9,498,561 B2 | 11/2016 | Kasuga et al. | |
| 9,539,365 B2 | 1/2017 | Kasuga et al. | |
| 9,730,982 B2 | 8/2017 | McKay et al. | |
| 9,731,052 B2 | 8/2017 | Kaplan et al. | |
| 2004/0022869 A1* | 2/2004 | Chen | A61P 29/00 424/623 |
| 2005/0074877 A1* | 4/2005 | Mao | A61L 27/3821 435/366 |
| 2005/0084513 A1 | 4/2005 | Tang | |
| 2005/0226856 A1 | 10/2005 | Ahlfors | |
| 2006/0040878 A1 | 2/2006 | Suddaby | |
| 2008/0124766 A1 | 5/2008 | Kuboki et al. | |
| 2008/0125390 A1 | 5/2008 | Metcalfe et al. | |
| 2010/0119564 A1 | 5/2010 | Kasuga et al. | |
| 2010/0145469 A1* | 6/2010 | Barralet | A61L 27/10 623/23.56 |
| 2010/0272776 A1 | 10/2010 | Harlow et al. | |
| 2011/0027181 A1* | 2/2011 | Amodei | A61L 27/54 424/9.1 |
| 2011/0076665 A1 | 3/2011 | Gatenholm et al. | |
| 2011/0112654 A1 | 5/2011 | Faldt | |
| 2011/0282465 A1* | 11/2011 | Desai | A61L 27/56 623/23.61 |
| 2012/0136090 A1 | 5/2012 | Kasuga et al. | |
| 2012/0190634 A1 | 7/2012 | Chung et al. | |
| 2012/0219595 A1 | 8/2012 | Ota et al. | |
| 2013/0195802 A1 | 8/2013 | Moore | |
| 2014/0242186 A1 | 8/2014 | Kasuga et al. | |
| 2015/0165092 A1 | 6/2015 | Kaplan et al. | |
| 2016/0052984 A1 | 2/2016 | Wozney et al. | |
| 2016/0121024 A1 | 5/2016 | Kasuga et al. | |
| 2018/0008418 A1* | 1/2018 | Bonutti | A61L 27/04 |
| 2019/0021862 A1 | 1/2019 | Kalpakci et al. | |

FOREIGN PATENT DOCUMENTS

| | | |
|---|---|---|
| WO | WO200108714 | 2/2001 |
| WO | WO2010052814 | 5/2010 |
| WO | WO2016159240 | 2/2018 |

OTHER PUBLICATIONS

Raggatt, LJ, et al. "Fracture Healing via Penosteal Callus Formation Requires Macrophages for Both Initiation and Progression of Early Endochondral Ossification", American Journal of Pathology, 2014, last accessed Oct. 7, 2019 at https://www.ncbi.nlm.nih.gov/pubmed/25285719.

Chan, JK, et al. "Low-dose TNF augments fracture healing in normal and osteoporotic bone by up-regulating the innate immune response", EMBO Mol Med, May 2015, last accessed Oct. 7, 2019 at https://www.ncbi.nlm.nih.gov/pubmed/25770819.

Schlundt, Claudia et al. "Macrophages in bone fracture healing: Their essential role in endochondral ossification," Bone (Oct. 2015), Medical University of Vienna, Edzhem Chavush, Department of Thoracic Surgery, https://josr-online.biomedcentral.com/track/pdf/10.1186/s13018-018-0926-7.

Zhang, Ran, et al. "M2 macrophages are closely associated with accelerated clavicle fracture healing in patients with traumatic brain injury: a retrospective cohort study", Journal of Orthopaedic Surgery and Research (2018) 13:213, https://www.meduniwien.ac.at/hp/fileadmin/thoraxchirurgie/applied-immunology/Students_information/.

Loi, Florence et al. "The effects of immunomodulation by macrophage subsets on osteogenesis in vitro", Stem Cell Research & Therapy 7:15, Departement of Orthopaedic Surgery, Stanford University School of Medicine, Stanford, CA 94305, 2016, pp. 1-11.

Schlundt, Claudia et al. "Macrophages in bone fracture healing: Their essentila role in endochondral ossification", Science Direct Journals, vol. 106, Jan. 2018, pp. 78-89, https://www.sciencedirect.com/science/article/pii/S8756328215003920; last accessed Jul. 10, 2019.

Ginaldi, Lia et al. "Osteoimmunology and Beyond", Current Medicinal Chemistry, 2016, 23, pp. 3754-3774.

Roberts, Timothy et al. "Bone grafts, bone substitutes and orthobiologics: The bridge between basic science and clinical advancements in fracture healing", Division of Orthopaedic Surgery; Albany Medical Center; Albany, NY USA, Organogenesis 8:4, Oct./Nov./Dec. 2012, Landes Bioscience, pp. 114-124.

Zheng, Zhi-wei et al. "Development of an Accurate and Proactive Immunomodulatory Strategy to Improve Bone Substitute Material-Mediated Osteogenesis and Angiogenesis", Theranostics 2018, vol. 8, Issue 19, pp. 5482-5500.

Raggatt, Liza J. et al. "Fracture Healing via Periosteal Callus Formation Required Macrophages for Both Initiation and Progression of Early Endochondral Ossification", The American Journal of Pathology, vol. 184, No. 12, Dec. 2014, pp. 1-14.

* cited by examiner

EXTENDED RELEASE IMMUNOMODULATORY IMPLANT TO FACILITATE BONE MORPHOGENESIS

FIELD

The present disclosure relates to the nascent field of osteoimmunology and to the field of bone morphogenesis, and more particularly to an implant that activates the innate immune system in a sequential timed fashion to initiate and enhance bone healing and regeneration or fusion.

BACKGROUND

In 2002, bone morphogenic protein (BMP) or recombinant human bone morphogenic protein-2 (rhBMP-2) was approved by the United States Food and Drug Administration (FDA) for fusion of the lumbar spine. The recommended application involved applying rhBMP-2 to collagen sponges and grafting them on to spinal vertebrae to facilitate spinal fusion.

While initially deemed as safe and without complication, widespread "on label" and "off label" use revealed numerous complications and adverse events including heterotrophic ossification, osteolysis, bone cyst formation, dysphagia, seroma, arachnoiditis, retrograde ejaculation, and increased neurologic deficits largely secondary to the severe inflammatory reaction that ensues when pharmacologic doses (as much as 1000 times over normal) are used to potentiate what is generally a well-orchestrated biologic event, that of normal bone healing.

While it is desirable to facilitate bony fusion in many instances requiring orthopedic surgery, the time-honored way has been the use of autologous bone (patient's own bone) to accomplish this endeavor. Since autologous bone harvesting is itself not without complication, including hemorrhage, infection, scarring, adjacent tissue damage, and persistent pain at the harvest site, alternative measures to facilitate rapid and robust bone healing have been coveted by orthopedic surgeons to treat conditions requiring bone healing or fusion. The main desire, of course, is a product which facilitates rapid and complete healing without the deleterious effects of autologous bone harvesting and without the numerous complications of bone graft enhancers such as BMP. While allograft and xenograft bone have been used, as well as specially prepared forms of these products, concerns over disease transmission by prions which are resistant to thermal, chemical, and radiation sterilization techniques still are of concern.

Thus, there is a long felt need in the art and science of orthopedic surgery for a product, means, and method for a graft or grafts facilitating bone fusion or healing, which does not require autologous harvesting of tissue, does not require potentially disease carrying allograft or xenograft products, and does not require pharmacologic doses of expensive biologic stimulants to orchestrate what is or should be a largely natural process.

SUMMARY

According to aspects illustrated herein, there is provided an extended release immunomodulatory implant operatively arranged to facilitate bone morphogenesis, comprising an inner portion including one or more interleukins, and an outer portion including an immunomodulatory stimulant such as an antigen.

According to aspects illustrated herein, there is provided an extended release immunomodulatory implant operatively arranged to facilitate bone morphogenesis, comprising an implant matrix including a first material, the implant matrix including an inner portion including at least one of interleukin 4, interleukin 10, and interleukin 13, and an outer portion including at least one of lipopolysaccharide and lipoteichoic acid.

According to aspects illustrated herein, there is provided a method of manufacturing an extended release immunomodulatory implant operatively arranged to facilitate bone morphogenesis, the method comprising forming an inner portion of the implant of a first material, applying at least one of interleukin 4, interleukin 10, and interleukin 13 to the inner portion, forming an outer portion of the implant of a second material, the outer portion enclosing the inner portion, and applying at least one of lipopolysaccharide and lipoteichoic acid to the outer portion.

According to aspects illustrated herein, there is provided an extended release immunomodulatory implant operatively arranged to facilitate bone morphogenesis, comprising an inner portion comprising an implant matrix including interleukin 10 and 13 at 10 ng/ml, an inner layer arranged around the inner portion, the inner layer comprising an implant matrix including interleukin 4 at 10 ng/ml, and an outer layer arranged around the inner layer, the outer layer comprising an implant matrix including an antigen or antigen mixture (for example lipopolysaccharide, lipoteichoic acid, and/or interferon gamma) at 40 ng/ml.

According to aspects illustrated herein, there is provided an extended release immunomodulatory implant operatively arranged to facilitate bone morphogenesis, comprising a core (or inner portion) comprising hydroxyapatite, a first layer arranged around the core, the first layer comprising beta-tricalcium phosphate including one or more interleukins (for example interleukin 4, 10, and/or 13), and a second layer arranged around the first layer, the second layer comprising beta-tricalcium phosphate including an antigen or antigen mixture (for example lipopolysaccharide, lipoteichoic acid, and/or interferon gamma). In some embodiments, the core, the first layer, and the second layer are 3D printed and include one or more predetermined porosities. For example, the core comprises a first porosity, the first layer comprises a second porosity, and the second layer comprises a third porosity.

According to aspects illustrated herein, there is provided an extended release immunomodulatory implant operatively arranged to facilitate bone morphogenesis, comprising a first component including at least one of inert beta-tricalcium phosphate, calcium carbonate, silicon, polylactic-co-glycolic acid, allograft bone, autograft bone, titanium, polyether ether ketone, and a mixture applied to the first component, the mixture including at least one of lipopolysaccharide and lipoteichoic acid.

It is an object of the present disclosure to provide a graft implant which facilitates a rapid and robust restoration, healing, or osseous union of selected bony elements requiring fusion or bony repair to restore integrity of a bony element, repair a large bony defect, or affix bony elements together for therapeutic purposes (i.e., bone fusion).

It is also an object of the present disclosure to not require the harvest of autologous products, such as bone cortex, bone marrow, blood, stem cells, platelets, or the like.

Additionally, it is an object of the present disclosure that no allograft, xenograft, coral, donor stem cells, or any similar products be used to eliminate graft to host disease transmission.

It is also an object of the present disclosure to avoid pharmacologic doses of cellular signaling proteins or molecules, thereby reducing the prospects of deleterious side effects already known in the art and science of bone healing.

It is also an object of the present disclosure that the graft is cost effective such that the graft implant could be utilized even in developing countries challenged by the ever-rising costs of modern medicine.

It is also an object of the present disclosure to provide a patterned sequence of growth and differentiation factors such as cytokines, enzymes, immunomodulatory molecules, or similar complexes arranged in an array to sequentially stimulate in a biomimetic fashion the normal cascade of reparative bone morphogenesis thereby facilitating, fostering or formulating accelerated bone growth, bone formation, bone healing and bone fusion for therapeutic purposes.

To achieve these objects, an implant or graft made of porous or fibrillary hydroxyapatite or beta tricalcium phosphate with 1% silicon by weight is chosen. This implant approximates the chemical makeup of normal bone but is devoid of any living elements. The size or volume of the implant will approximate the bone void to be filled or region to be grafted to facilitate the bony fusion.

The implant or graft comprises an outer layer or layers including lipopolysaccharide (LPS), lipoteichoic acid (LTA), interferon gamma, and/or other antigens or stimulants, which activate M0 and M1 macrophages. These substances can also chemotactically attract circulating and tissue monocytes, which in turn can be converted to M0 and M1 macrophages. In some embodiments, the outer layer is affixed with LPS and/or LTA. In some embodiments, LPS and/or LTA is adsorbed on the outer layer. In some embodiments, the outer layer is saturated or impregnated with LPS and/or LTA. In some embodiments, the LPA is derived from *Escherichia coli* (*E. coli*), such as, for example, *E. coli* Strain O55:B5. In some embodiments, the LTA is derived from *Staphylococcus aureus* (*S. aureus*).

The implant or graft further comprises an inner layer or recesses including interleukin 4, 10, or 13, either individually or in combination. In some embodiments, the inner layer is affixed with interleukin 4, 10, and/or 13. In some embodiments, interleukin 4, 10, and/or 13 is adsorbed on the inner layer. In some embodiments, the inner layer is saturated or impregnated with interleukin 4, 10, and/or 13. By arranging the layers such that the activating immunomodulatory substance(s) is outside (i.e., on the outer layer) and the cell signally molecules are arranged inside (i.e., on the inner layer), an immunomodulatory or "smart" implant is created, and one which more naturally replicates or coordinates normal bone healing, albeit by convincing the body's innate immune system that a contaminated compound fracture exists and is in need of biologic debridement and repair. The outer layer containing immunomodulatory molecules serves to initiate the activity of the innate immune system via pattern recognition of the LPS and/or LTA by receptors on monocytes and macrophages which bind these molecules. In some embodiments, alternatively, or in conjunction, interferon gamma could be used.

In some embodiments, the implant comprises a mixture of LPS and LTA ranging from 1 ng/ml to 1,000 ng/ml, with the preferred embodiment including 40 ng/ml. In some embodiments, the implant comprises interferon gamma ranging from 1 ng/ml to 1,000 ng/ml, with the preferred embodiment including 200 ng/ml. In some embodiments, the implant comprises interleukin 4 ranging from 0.1 ng/ml to 100 ng/ml with the preferred embodiment including 10 ng/ml. In some embodiments, the implant comprises interleukin 10 ranging from 0.1 ng/ml to 100 ng/ml with the preferred embodiment including 10 ng/ml. In some embodiments, the implant comprises interleukin 13 ranging from 0.1 ng/ml to 100 ng/ml with the preferred embodiment including 10 ng/ml.

Once monocytes or M0 macrophages bind to the immunomodulatory molecule, they release a cytokine(s) which attracts more monocytes and M0 macrophages, which in turn are drawn toward the implant via a chemotactic gradient. The immunomodulators (i.e., LPS and/or LTA) also facilitate the conversion of monocytes and M0 macrophages to M1 macrophages often referred to as classically activated macrophages, which in turn initiate the healing process. M1 macrophages aggressively phagocytose immune modulatory molecules and any tissue debris they are bound to until all of the immunomodulatory molecules are gone. In this process, the thin outer layer of the implant is removed by the M1 macrophages exposing the deeper layer of denser beta-tricalcium phosphate and/or hydroxyapatite containing interleukins. Interleukins (particularly interleukin 4) are a potent stimulant that converts the M1 (inflammatory or classically activated) macrophage into an M2 (reparative or alternately activated) macrophage, which begins the reparative process. The M1 to M2 conversion is further enhanced by the lack of LPS and/or LTA and the presence of calcium ions in directing the need for bone repair.

By layering the activating components in this fashion, the implant serves multiple purposes and rises above the level of serving as a simple tissue scaffold. Indeed, the implant attracts, activates, and ultimately converts circulating or resident monocytes and macrophages into participating in what is essentially an artificial bone repair.

LPS, LTA, and other immunomodulators are potent stimulants of the innate immune system. Their presence suggests an invasion by foreign organisms and they are actively phagocytized by M1 macrophages, which in turn chemotactically attract other monocytes and macrophages to the area as part of the initial scene of fracture repair. M0 macrophages can be converted to M1 macrophages by LPS and/or LTA; this is known as classic activation and is routinely done to study these cells.

M1 macrophages serve to kill bacteria, remove debris, and recruit circulating monocytes and resident tissue macrophages to do the same. They remain M1 or classically activated macrophages until the antigen (LPS and/or LTA) is gone. This stage of M1 activation is analogous to the inflammatory stage of fracture repair. These M1 macrophages are often known as inflammatory macrophages for this reason.

Once the antigenic threat no longer exists (i.e., the LPS and/or LTA is gone), M1 or classically activated macrophages metamorphose into M2 or alternatively activated macrophages, which are anti-inflammatory or reparative in nature. This transformation is facilitated by the presence of interleukin 4, 10, and 13, which is released by M1 macrophages once all antigen is disposed of and full restoration of bone and hence fracture repair is initiated, a process which is enhanced by calcium ions and silicon ions present in bone.

By having an implant constructed in such a layered fashion, the maximum capacity of the immunomodulatory aspect of bone healing can be harnessed and modulated to facilitate or orchestrate a rapid and robust bone healing process along its natural path.

Immunomodulatory molecules (LPS and/or LTA) suggest injury to the host involving invasion by pathogens. Surface receptors of monocytes and M0 macrophages encounter the immunomodulatory molecules and bind them to their surfaces. Monocytes and M0 macrophages release cytokines to attract more cells (i.e., monocytes and M0 macrophages) to the area to confront the pathogens and transform into M1 macrophages, which aggressively phagocytose the immunomodulatory molecules and bone fragments to which they are attached until the immunomodulatory molecules are gone. The lack of stimulation by LPS and/or LTA results in the M1 macrophages producing interleukins, which facilitates the transformation of M1 (inflammatory) macrophages into M2 (reparative) macrophages. In the presence of calcium ions, M1 macrophages also release Oncostatin M (OSM), prostaglandin E2 (PGE2), and BPMs, which are necessary to convert mesenchymal stem cells into osteoprogenitor cells, which invade the inner portion of the implant and initiate and coordinate bone morphogenesis.

For example, the implant is laid on the surface of two bony elements that have been decorticated in preparation for fusion. Wound blood and serum elute LPS from the surface or outer layer of the implant signaling the monocytes in blood to produce cytokines that attract additional monocytes and macrophages (M0 macrophages) to the area. These classically activated (M0) macrophages begin the process of neutralizing the bacterial invaders (antigen) by converting to M1 macrophages, as will be discussed in greater detail below, and remain activated until all antigen is removed from the outer layer of the implant.

Once the antigen load is negligible, classically activated M1 macrophages metamorphose into alternatively activated M2 macrophages, which are key in tissue repair. The activity of M2 macrophages is enhanced by interleukins 4, 10, and 13, which are encountered in the deeper layers or inner layer of the implant and a full repair process is instigated. M2 macrophages, in turn, activate adjacent tissue dendritic cells, mesenchymal stem cells, and osteoprogenitor cells, which become mature osteoblasts so that bony repair or fusion can rapidly progress.

Since avirulent activation of the immunomodulatory pathway was used, the deleterious effects of a true infection are avoided, much like a vaccination, with the killed or attenuated viruses having activated the adaptive immune system without having to suffer the disease. Once the innate immune system is activated and the cells come in contact with the calcium in the implant or graft, a normal healing process occurs with all of the necessary natural cell signals and the correct amounts needed to effect rapid bone morphogenesis and bone healing or fusion. Natural bone resorption, reconstitution, and osseointegration of the graft implant thereby occurs.

According to aspects illustrated herein, there is provided a synthetic implant of porous hydroxyapatite and/or beta-tricalcium phosphate containing immunomodulators which activate the innate immune system in a sequential timed fashion thereby initiating and enhancing bone healing or fusion, for example, in humans and animals.

According to aspects illustrated herein, there is provided an implant comprising a solid, particulate, and/or fibrillary hydroxyapatite and/or beta-tricalcium phosphate. The implant comprising an outer portion including absorbed or adsorbed antigen(s) of LPS and/or LTA, which activates the innate immune system and particularly M0 or M1 macrophages, which can instigate bone morphogenesis and repair. It should be appreciated that other antigens suitable for activating the innate immune system may be used, and that this disclosure should not be limited to only the use of LPS and LTA. Furthermore, a concentration of antigen suitable to classically activate macrophages could be used. In some embodiments, interferon gamma may be used to activate the innate immune system.

Once the implant activates the innate immune system, all of the natural products necessary to affect bone morphogenesis or bone healing are activated and brought to the surgical site through natural cell signaling. Upon removal of the antigen load from the surface or outer portion of the implant, classically activated M1 macrophages transform to reparative or M2 macrophages. This conversion is more rapidly facilitated by interleukin 4, 10, and/or 13 encountered in deeper layers or an inner portion of the implant. In some embodiments, the inner layers or portion of the implant are less porous (and more dense) than the outer layers or portion.

Once M2 or alternatively activated macrophage conversion occurs, full bone morphogenesis and healing or fusion progresses until the implant is transformed into normal bone and fusion of bony elements is complete. Macrophages (M1 and M2) furthermore release cytokines (OSM, PGE2, and BMPs), which attract mesenchymal stem cells and osteoprogenitor cells into the graft. These cells inhabit the inner layers or portions of the implant or graft and transform into mature osteoblasts, which facilitate bone morphogenesis. In some embodiments, the implant is 3D printed and comprises variations in porosity of the layers, with the outer layer or portion being the most porous and the inner layer or portion being most dense, such that structural integrity of the implant can be maintained when the outer layer or portion is removed by M1 macrophages and ultimately remodeled by osteoclast and osteoblast activity. In some embodiments, the implant comprises electrospun beta-tricalcium phosphate fibers, the porosity of which can be varied by their compactness.

The implant of the present invention adds another dimension to what is already known. Since the LPS and/or LTA elutes from the surface of the implant, and since the elutant has the capacity to attract monocytes and M0 macrophages chemotactically, it becomes "osteopreparatory" by virtue of direct chemotaxis by the elutant and by virtue of the fact that any monocytes, monocyte derived cells, or neutrophils that come in contact with the antigen will further release cytokines to attract more monocytes and M0 macrophages and enhance their conversion or transformation to M1 macrophages as part of the innate immune response to bodily injury and invasion by pathogens (e.g., a classic compound fracture). By having the implant made of calcium based material, another requirement is fulfilled. Calcium ions are an important signal to cells that bone is involved in the trauma and that bone repair will be required. This is not critical at the macrophage level, but when the macrophages have done their work, the calcium component is important in signaling mesenchymal stem cells and osteoprogenitor cells to lay down bone.

Ultimately, it is the M2 macrophage that signals the stem and progenitor cells to begin, but calcium is needed for them to carry out normal bone formation. The M1 to M2 conversion is facilitated by the interleukins in the inner layer (e.g., interleukins 4, 10, and/or 13) and the M2 cells set the stage for and facilitate the performance of the mesenchymal stem cells and osteoprogenitor cells to direct morphogenesis toward mature osteoblasts, which form mature bone.

In essence, therefore, the present disclosure provide for an implant that is unique in regenerative bone biology. The implant is osteopreparatory, osteoinductive, and osteoconductive. At present, in the art, most bone grafts are only osteoconductive with a few, including autograft bone, being both osteoconductive and osteoinductive. Additionally, the implant orchestrates bone morphogenesis in a controlled, sequential, and logical fashion whereby the cellular participants are exploited to their maximal value to achieve rapid bone repair and healing. No outside cells are required since the organisms own innate healing powers are directed and enhanced by employing the innate immune system to facilitate the process. Since the innate immune system evolved hundreds of million years ago, this implant and process has implications for all animals, not just humans. Any animal with a bony skeleton could benefit from this healing method. Furthermore, the implant is designed to dissolve completely, leaving no trace of itself or its constituent components. Only normal regenerative bone is left behind.

Consider, therefore, the implant is placed in a surgical site having an excoriated or prepared surface (e.g., decorticated bone). The outer layer of the implant elutes LPS/LTA, which chemotactically attracts monocytes, neutrophils, and M0 macrophages. The monocytes and macrophages imbibe the LPS/LTA and destroy them with lysosomes. This action releases cytokines, which further attract more monocytes and M0 macrophages to the site in every increasing numbers. LPS/LTA further transforms monocytes and M0 macrophages into M1 or inflammatory macrophages, also known as classically activated macrophages, which dissolve the outer layer of the implant to which the antigen is absorbed or adsorbed. This "clean up" process continues until all of the outer layer and the LPS/LTA associated with it is completely gone. The M1 macrophages then encounter the inner layer to which is absorbed or affixed, interleukin 4. Interleukin 4 signals the M1 macrophage or inflammatory cell to become a M2 macrophage or anti-inflammatory cell, also known as a reparative cell, or alternatively activated macrophage. The absence of LPS/LTA also favors this transformation. M2 macrophages start the tissue reparative process using the hydroxyapatite or beta tricalcium phosphate of the inner layer as the scaffold on which the repair process using the hydroxyapatite or beta tricalcium phosphate of the inner layer as the scaffold on which the repair process is performed. M2 macrophages in turn, chemotactically attract mesenchymal stem cells, dendritic cells, and osteoprogenitor cells into the scaffolding of the implant to facilitate further bone morphogenesis. Thus, the implant of the present disclosure is osteopreparatory, osteoinductive, osteoconductive, and naturally dissolves leaving pure normal regenerative bone behind.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

Figure 1:
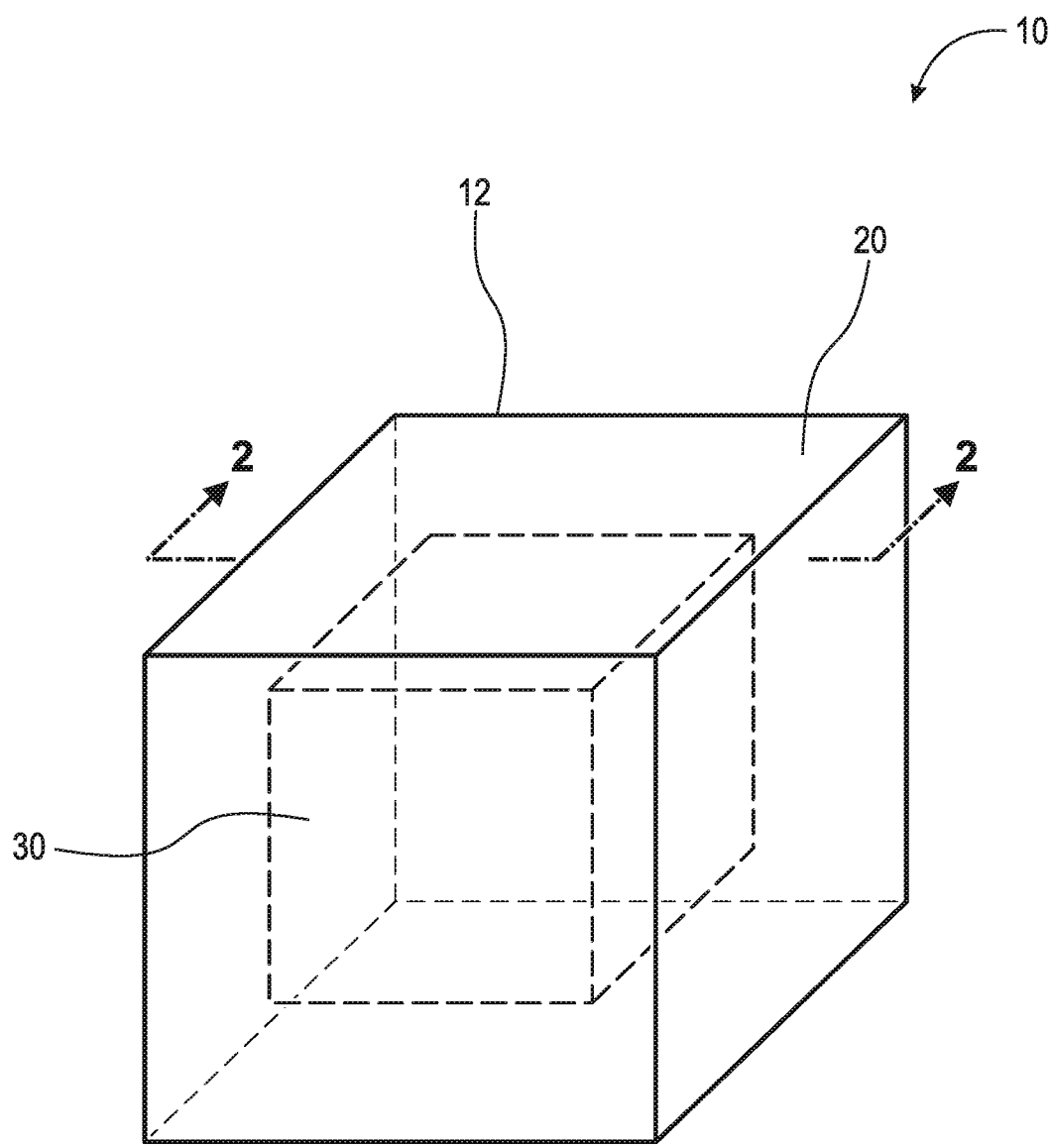
FIG. 1 is a perspective view of an implant.
Figure 2:
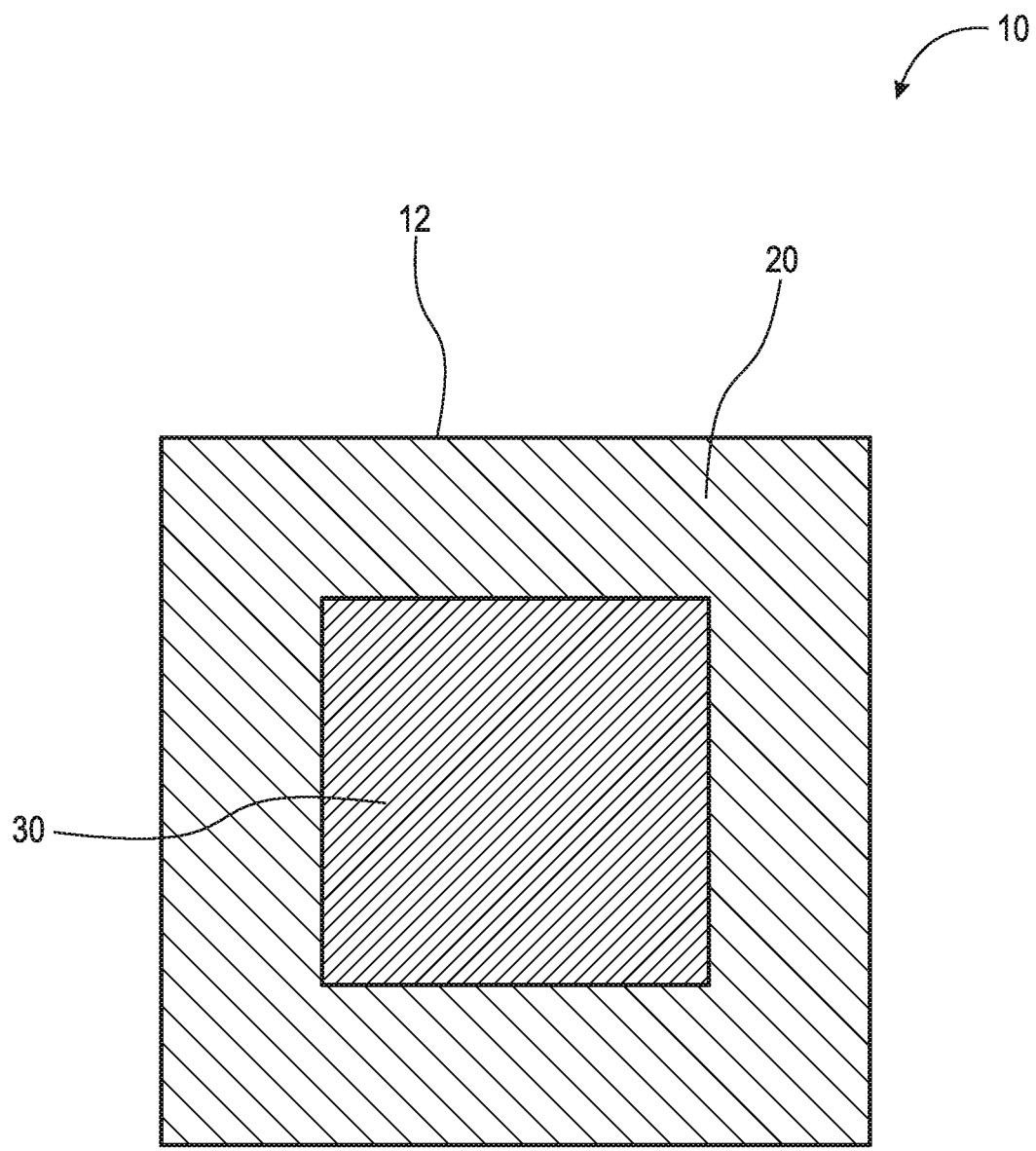
FIG. 2 is a cross-sectional view of the implant taken generally along line 2-2 in FIG. 1.

Referring now to the figures, FIG. 1 is a perspective view of implant 10. FIG. 2 is a cross-sectional view of implant 10 taken generally along line 2-2 in FIG. 1. Implant 10 generally comprises implant matrix 12 which includes outer portion(s) or layer(s) 20 and inner portion(s) 30. Implant matrix 12 comprises inert beta-tricalcium phosphate, calcium carbonate (CaCO3), silicon, polylactic-co-glycolic acid (PLGA), and/or hydroxyapatite. In some embodiments, implant matrix 12 consists of inert beta-tricalcium phosphate, CaCO3, silicon, and PLGA. In some embodiments, implant matrix 12 consists of inert beta-tricalcium phosphate, CaCO3, silicon, and PLGA with silicon at 1% by weight. In some embodiments, implant matrix 12 comprises allograft bone, autograft bone, xenograft bone, a titanium implant, a polyether ether ketone (PEEK) implant, and/or synthetic bone void filler coated and/or impregnated with the antigen or antigen mixture (LPS, LTA, and/or other suitable antigen) and/or interleukins 4, 10, and/or 13. By impregnated, it is meant that the implant (e.g., the inner or outer portions) is filled, imbued, permeated, or saturated with the antigen or antigen mixture and/or interleukins. It should be appreciated that implant 10, including inner portion 30 and outer layer 20, may comprise any suitable geometry, for example, cuboid, cube, sphere, cylinder, cone, tetrahedron, triangular prism, etc., and that the present disclosure should not be limited to the geometric shape(s) shown in the figures. The following description should be read in view of FIGS. 1-2.

Outer portion or layer 20 comprises LPS, LTA, and/or other suitable antigen, and as discussed above, is operatively arranged to attract monocytes and macrophages to the site via chemotaxis and initiate the M1 phase of macrophages. Specifically, outer portion 20 attracts monocytes and macrophages to the site, and once there, converts M0 macrophages into M1 macrophages, which phagocytose outer portion 20. As such, outer portion 20 is phagocytosable, or capable of being phagocytosed. Put another way, outer portion 20 is operatively arranged to be completely removable from inner portion 30 via phagocytosis. In some embodiments, outer portion 20 is operatively arranged to be partially removable from inner portion 30. In such embodiments, M1 macrophages phagocytize the antigen on or in implant matrix 12 and access inner portion(s) 30 through holes and/or porosities in outer portion 20, thus leaving behind the porous implant matrix 12 (e.g., inert beta-tricalcium phosphate, CaCO3, silicon, PLGA, hydroxyapatite, allograft bone, autograft bone, xenograft bone, a titanium implant, a PEEK implant, and/or synthetic bone void filler). In some embodiments, outer portion 20 consists of a mixture of LPS and LTA. In some embodiments, outer portion 20 consists of a mixture of 50% by weight LPS and 50% by weight LTA. In some embodiments, outer portion 20 consists of a mixture of 50% by weight LPS and 50% by weight LTA, mixed together at a concentration of 5 micrograms per liter each. In some embodiments, outer portion 20 consists of a mixture of 50% by weight LPS and 50% by weight LTA, mixed together at a concentration of 5 micrograms per liter each, wherein the LPS is derived from *E. coli* (e.g., *E. coli* Strain O55:B5) and the LTA is derived from *S. aureus*. In some embodiments, outer portion 20 comprises an antigen or antigen mixture of 40 ng/ml. It is also recognized that 100% LPS or 100% LTA or similar antigen can be used. Indeed, any combination of stimulants known to specifically activate the innate immune system can be employed.

Outer portion 20 may comprise an antigen or antigen mixture (LPS, LTA, and/or other suitable antigen) completely, or inert beta-tricalcium phosphate, CaCO3, silicon, PLGA, and/or hydroxyapatite with the antigen or antigen mixture applied thereon or embedded or injected therein. In some embodiments, the antigen or antigen mixture (LPS, LTA, and/or other suitable antigen) is added to implant 10 to create outer portion 20 by dipping implant 10 therein and air drying. In some embodiments, the antigen or antigen mixture (LPS, LTA, and/or other suitable antigen) is added to implant 10 to create outer portion 20 by placing implant 10 (e.g., in the wound or incision) and squirting the antigen or antigen mixture thereon.

Inner portion 30 may comprise an infusion of interleukins, and as discussed above, is operatively arranged to initiate the M2 phase of macrophages. In some embodiments, inner portion 30 comprises an infusion of capsaicin and/or interleukins. Once the M1 macrophages completely and/or partially phagocytoses outer portion 20 (i.e., all of the LPS, LTA, and/or other suitable antigen is eaten away), the M1 macrophages encounter inner portion 30, which comprises interleukins 4, 10, and/or 13, and are converted to M2 macrophages. The M2 macrophages begin the reparative process and hence bony repair or fusion. M1 macrophages are converted to M2 macrophages through contact with inner portion 30 (i.e., the interleukins). Additionally, once the M1 macrophages completely and/or partially phagocytize outer portion 20 (i.e., the antigen or antigen mixture), interleukins are released by the M1 macrophages to initiate the M2 phase of macrophages, based in part on the dwindling amounts of antigen left to phagocytose. Thus, implant 10 can convert M1 macrophages to M2 macrophages in two ways: 1) after M1 macrophages completely phagocytize outer portion 20; and, 2) when M1 macrophages come into contact with inner portion 30. In some embodiments, inner portion 30 comprises interleukin 4, 10, and/or 13.

In some embodiments, implant matrix 12 comprises beta-tricalcium phosphate, for example, 3D printed such that inner portion 30 comprises small pore sizes and outer portion 20 comprises larger pore sizes. The larger pores and reduced density of outer portion 20 allows it to be infused with the antigen or antigen mixtures (LPS, LTA, and/or other suitable antigen) to chemotactically attract M0 and M1 macrophages and monocytes. The porosity and reduced density of outer portion 20 also speeds the process of phagocytosis, wherein the M1 macrophages phagocytose outer portion 20 until it is gone and only inner portion 30 remains. In some embodiments, and as previously discussed, outer portion 20 is operatively arranged to be partially removable/dissolvable, wherein the M1 macrophages phagocytose the antigen on or in implant matrix 12 and subsequently access inner portion 30 through holes or pores in outer portion 20. The smaller pores and increased density of inner portion 30, which contains the interleukins, slows its dissolution so as to remain until suitable bone growth or fusion has occurred or is occurring. In some embodiments, inner portion(s) 30 comprises a porosity having an average pore size of 50-200 microns, and the outer portion(s) 20 comprises a porosity having an average pore size of 200-500 microns. In some embodiments, the pores of inner portion(s) 30 and outer portion(s) 20 are interconnected by channels throughout implant 10.

Implant 10 generally acts as a dissolving implant or a time release bone fusion capsule or implant. The M0 macrophages are attracted to implant 10 and converted to M1 macrophages upon arrival. The M1 macrophages "dissolve" or phagocytize outer portion 20 comprising the antigen or antigen mixture (LPS, LTA, and/or other suitable antigen) and, once this is done, the M1 macrophages encounter the denser inner portion 30 containing interleukins. Inner portion 30 containing interleukins modulates the transition of M1 or inflammatory macrophages to M2 or anti-inflammatory macrophages thereby facilitating the reparative process (i.e., bone growth or fusion). Implant 10 is eventually incorporated and transformed into normal regenerative bone by actively orchestrating the key cellular actors involved in bone healing.

Figure 3:
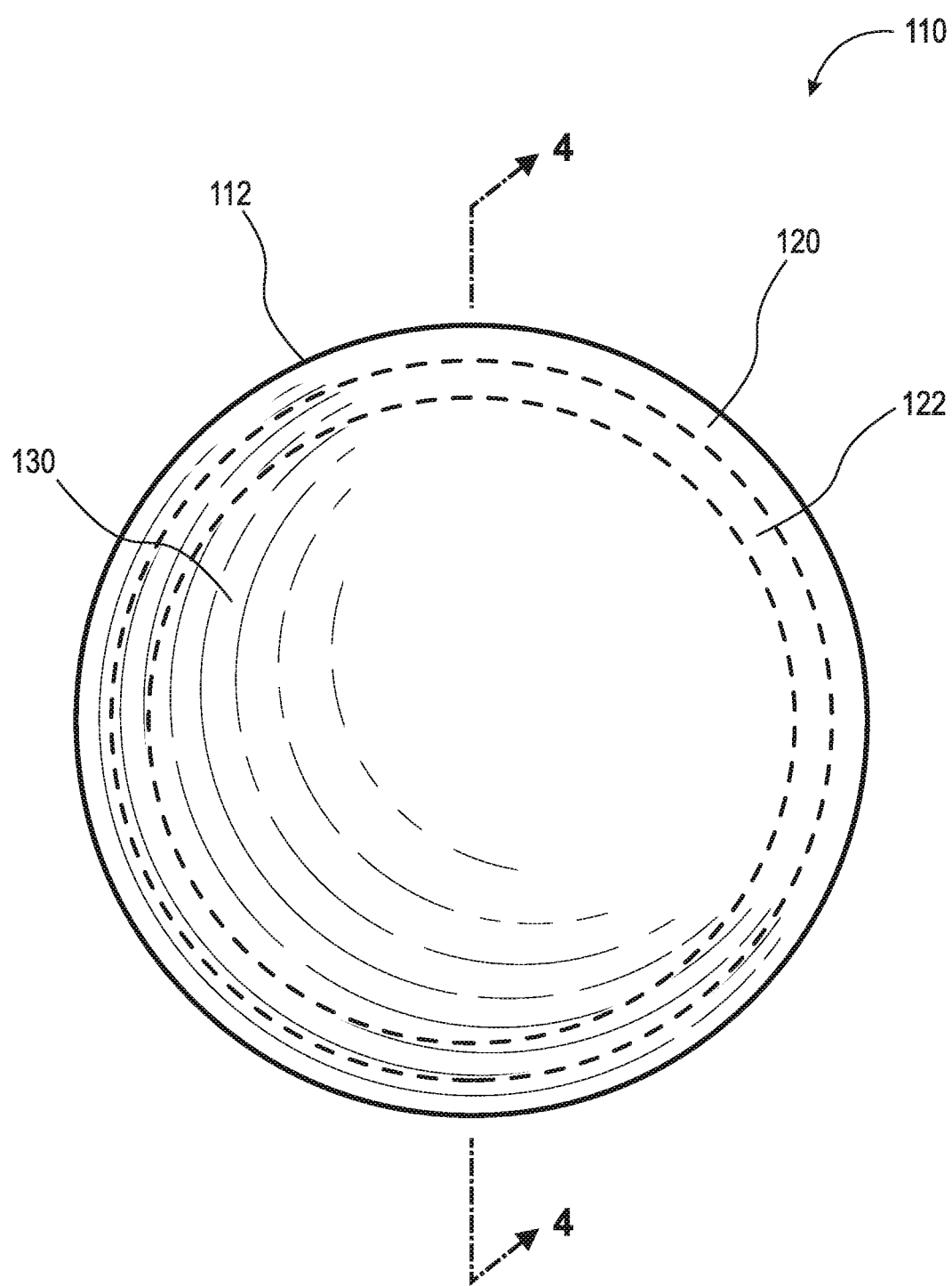
FIG. 3 is a perspective view of an implant.
Figure 4:
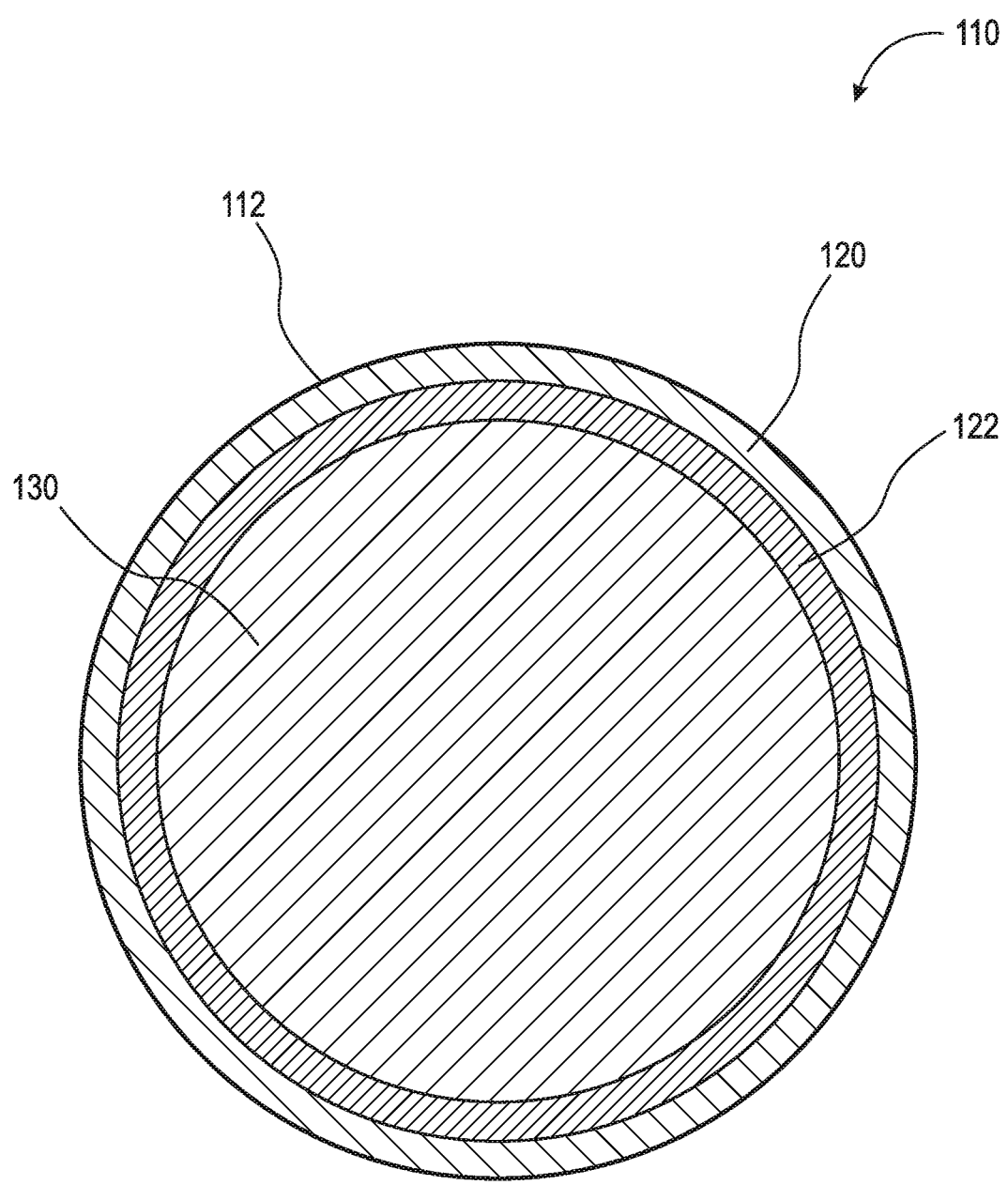
FIG. 4 is a cross-sectional view of the implant taken generally along line 4-4 in FIG. 3.

FIG. 3 is a perspective view of implant 110. FIG. 4 is a cross-sectional view of implant 110 taken generally along line 4-4 in FIG. 3. Implant 110 generally comprises implant matrix 112 which includes outer layer(s) 120, inner layer(s) 122, and inner portion(s) 130. Implant matrix 112 comprises inert beta-tricalcium phosphate, CaCO3, silicon, PLGA, and/or hydroxyapatite. In some embodiments, implant matrix 112 consists of inert beta-tricalcium phosphate, CaCO3, silicon, and PLGA. In some embodiments, implant matrix 112 consists of inert beta-tricalcium phosphate, CaCO3, silicon, and PLGA with silicon at 1% by weight. In some embodiments, implant matrix 112 comprises inert beta-tricalcium phosphate or hydroxyapatite alone. In some embodiments, implant matrix 112 comprises allograft bone, autograft bone, xenograft bone, a titanium implant, a polyether ether ketone (PEEK) implant, and/or synthetic bone void filler coated and/or impregnated with the antigen or antigen mixture (LPS, LTA, and/or other suitable antigen) and/or interleukins 4, 10, and/or 13. By impregnated, it is meant that the implant (e.g., the inner or outer portions) is filled, imbued, permeated, or saturated with the antigen or antigen mixture and/or interleukins. It should be appreciated that implant 110, including inner portion 130 and layers 120 and 122, may comprise any suitable geometry, for example, cuboid, cube, sphere, cylinder, cone, tetrahedron, triangular prism, etc., and that the present disclosure should not be limited to the geometric shape(s) shown in the figures. The following description should be read in view of FIGS. 3-4.

Outer layer 120 comprises LPS, LTA, and/or other suitable antigen, and as discussed above, is operatively arranged to attract monocytes and macrophages to the site via chemotaxis and initiate the M1 phase of macrophages. Specifically, outer layer 120 attracts monocytes and macrophages to the site, and once there, converts M0 macrophages into M1 macrophages, which phagocytose outer layer 120. As such, outer layer 120 is phagocytosable, or capable of being phagocytosed. Put another way, outer layer 120 is operatively arranged to be completely removable from inner layer 122 and inner portion 130 via phagocytosis. In some embodiments, outer layer 120 and/or inner layer 122 are operatively arranged to be partially removable from inner portion 130. In such embodiments, M1 macrophages phagocytize the antigen on or in bone matrix 112 and access inner portion 130 through holes and/or porosity in outer layer 120 and/or inner layer 122, thus leaving behind the porous bone matrix 112 (e.g., inert beta-tricalcium phosphate, CaCO3, silicon, PLGA, hydroxyapatite, allograft bone, autograft bone, xenograft bone, a titanium implant, a PEEK implant, and/or synthetic bone void filler). In some embodiments, outer layer 120 consists of a mixture of LPS and LTA. In some embodiments, outer layer 120 consists of a mixture of 50% by weight LPS and 50% by weight LTA. In some embodiments, outer layer 120 consists of a mixture of 50% by weight LPS and 50% by weight LTA, mixed together at a concentration of 5 micrograms per liter each. In some embodiments, outer layer 120 consists of a mixture of 50% by weight LPS and 50% by weight LTA, mixed together at a concentration of 5 micrograms per liter each, wherein the LPS is derived from E. coli (e.g., E. coli Strain O55:B5) and the LTA is derived from S. aureus. In some embodiments, outer layer 120 comprises an antigen or antigen mixture of 40 ng/ml. It is recognized that 100% LPS or 100% LTA or 100% of any antigen or any combination thereof can be chosen to optimally activate the innate immune system.

Outer layer 120 may comprise an antigen or antigen mixture (LPS, LTA, and/or other suitable antigen) completely, or inert beta-tricalcium phosphate, CaCO3, silicon, PLGA, and/or hydroxyapatite with the antigen or antigen mixture applied thereon or embedded or injected therein. In some embodiments, the antigen or antigen mixture (LPS, LTA, and/or other suitable antigen) is added to implant 110 to create outer layer 120 by dipping implant 110 therein and air drying. In some embodiments, the antigen or antigen mixture (LPS, LTA, and/or other suitable antigen) is added to implant 110 to create outer layer 120 by placing implant 110 (e.g., in the wound or incision) and squirting the antigen or antigen mixture thereon. The antigen or antigen mixture could also be added at any point as part of the 3D printing process in the manufacturing of the implant.

Inner layer 122 comprises LPS, LTA, and/or other suitable antigen, and as discussed above, is operatively arranged to attract monocytes and macrophages to the site via chemotaxis and initiate the M1 phase of macrophages. Specifically, inner layer 122 attracts monocytes and macrophages to the site, and once there, converts M0 macrophages into M1 macrophages, which phagocytose outer layer 120 and subsequently inner layer 122. As such, outer layer 120 and inner layer 122 are phagocytosable, or capable of being phagocytosed. Put another way, outer layer 120 and inner layer 122 are operatively arranged to be completely removable from inner portion 130 via phagocytosis. In some embodiments, outer layer 120 and/or inner layer 122 are operatively arranged to be partially removable from inner portion 130. In such embodiments, M1 macrophages phagocytize the antigen on or in bone matrix 112 and access inner portion 130 through holes and/or porosity in outer layer 120 and/or inner layer 122, thus leaving behind the porous bone matrix 112 (e.g., inert beta-tricalcium phosphate, CaCO3, silicon, PLGA, hydroxyapatite, allograft bone, autograft bone, xenograft bone, a titanium implant, a PEEK implant, and/or synthetic bone void filler). In some embodiments, inner layer 122 consists of a mixture of LPS and LTA. In some embodiments, inner layer 122 consists of a mixture of 50% by weight LPS and 50% by weight LTA. In some embodiments, inner layer 122 consists of a mixture of 50% by weight LPS and 50% by weight LTA, mixed together at a concentration of 5 micrograms per liter each. In some embodiments, inner layer 122 consists of a mixture of 50% by weight LPS and 50% by weight LTA, mixed together at a concentration of 5 micrograms per liter each, wherein the LPS is derived from E. coli (e.g., E. coli Strain O55:B5) and the LTA is derived from S. aureus. It is recognized that 100% LPS or 100% LTA or 100% of any antigen or any combination thereof can be chosen to optimally activate the innate immune system.

Inner layer 122 may comprise an antigen or antigen mixture (LPS, LTA, and/or other suitable antigen) completely, or inert beta-tricalcium phosphate, CaCO3, silicon, PLGA, and/or hydroxyapatite with the antigen or antigen mixture applied thereon or embedded or injected therein. In some embodiments, the antigen or antigen mixture (LPS, LTA, and/or other suitable antigen) is added to implant 110 to create inner layer 122 by dipping implant 110 therein and air drying. In some embodiments, the antigen or antigen mixture (LPS, LTA, and/or other suitable antigen) is added to implant 110 to create inner layer 122 by placing implant 110 (e.g., in the wound or incision) and squirting the antigen or antigen mixture thereon. The antigen or antigen mixture could also be added at any point as part of the 3D printing process in the manufacturing of the implant.

In some embodiments, inner layer 122 may comprise an infusion of interleukins, as discussed above, and is operatively arranged to initiate the M2 phase of macrophages. In some embodiments, inner layer 122 comprises an infusion of capsaicin and/or interleukins. Once the M1 macrophages completely and/or partially phagocytose outer layer 120 (i.e., all of the LPS, LTA, and/or other suitable antigen is eaten away), the M1 macrophages encounter inner layer 122, which comprises interleukins 4, 10, and/or 13, and are converted to M2 macrophages. The M2 macrophages begin the reparative process and hence bony repair or fusion. M1 macrophages are converted to M2 macrophages through contact with inner layer 122 (i.e., the interleukins). Additionally, once the M1 macrophages completely and/or partially phagocytize outer layer 120 (i.e., the antigen or antigen mixture), interleukins are released by the M1 macrophages to initiate the M2 phase of macrophages. Thus, implant 110 can convert M1 macrophages to M2 macrophages in two ways: 1) after M1 macrophages completely and/or partially phagocytize outer layer 120; and, 2) when M1 macrophages come into contact with inner layer 122. In some embodiments, inner layer 122 comprises interleukin 4 at 10 ng/ml.

Inner portion 130 may comprise an infusion of interleukins, and as discussed above, is operatively arranged to initiate the M2 phase of macrophages. In some embodiments, inner portion 130 comprises an infusion of capsaicin and/or interleukins. Once the M1 macrophages completely and/or partially phagocytose outer layer 120 and/or inner layer 122 (i.e., all of the LPS, LTA, and/or other suitable antigen is eaten away), the M1 macrophages encounter inner portion 130, which comprises interleukins 4, 10, and/or 13, and are converted to M2 macrophages. The M2 macrophages begin the reparative process and hence bony repair or fusion. M1 macrophages are converted to M2 macrophages through contact with inner portion 130 (i.e., the interleukins). Additionally, once the M1 macrophages completely and/or partially phagocytize outer layer 120 and/or inner layer 122 (i.e., the antigen or antigen mixture), interleukins are released by the M1 macrophages to initiate the M2 phase of macrophages. Thus, implant 110 can convert M1 macrophages to M2 macrophages in two ways: 1) after M1 macrophages completely and/or partially phagocytize outer layer 120 and/or inner layer 122; and, 2) when M1 macrophages come into contact with inner portion 130. In some embodiments, inner portion 130 comprises interleukin 10 and 13 at 10 ng/ml.

In some embodiments, implant matrix 112 comprises beta-tricalcium phosphate, for example, 3D printed such that inner portion 130 comprises small pore sizes and outer layer 120 and inner layer 122 comprise larger pore sizes. The larger pores and reduced density of outer layer 120 and inner layer 122 allows the layers to be infused with the antigen or antigen mixture (LPS, LTA, and/or other suitable antigen) to chemotactically attract M0 and M1 macrophages and monocytes. The porosity and reduced density of outer layer 120 and inner layer 122 also speeds the process of phagocytosis, wherein the M1 macrophages phagocytose outer layer 120 and/or inner layer 122 until they are gone or partially gone, and only inner portion 130 and/or inner layer 122 remain. In some embodiments, and as previously discussed, outer layer 120 and/or inner layer 122 are operatively arranged to be partially removable/dissolvable, wherein the M1 macrophages phagocytose the antigen on or in implant matrix 112 and subsequently access inner portion 130 through holes or pores in outer layer 120 and inner layer 122. The smaller pores and increased density of inner portion 130, which contains the interleukins, slows its dissolution so as to remain until suitable bone growth or fusion has occurred. In some embodiments, inner portion(s) 130 comprises a porosity having an average pore size of 50-200 microns, outer layers 120 comprises a porosity having an average pore size of 200-500 microns, and layer 122 comprises a porosity having an average pore size of 200-500 microns. In some embodiments, the pores of inner portion(s) 130 and outer layers 120 and 122 are interconnected by channels through implant 110.

Implant 110 generally acts as a dissolving implant or a time release bone fusion capsule or implant. The M0 macrophages are attracted to implant 110 and converted to M1 macrophages upon arrival. The M1 macrophages "dissolve" or phagocytize outer layer 120 and then inner layer 122, which comprise the antigen or antigen mixture (LPS, LTA, and/or other suitable antigen) and, once this is done, the M1 macrophages encounter the denser inner portion 130 containing interleukins. Inner portion 130 containing interleukins modulates the transition of M1 or inflammatory macrophages to M2 or anti-inflammatory macrophages thereby facilitating the reparative process (i.e., bone growth or fusion). Implant 110 is eventually incorporated and transformed into normal regenerative bone by actively orchestrating the key cellular actors involved in bone healing.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

10 Implant
12 Implant matrix
20 Outer portion
30 Inner portion
110 Implant
112 Implant matrix
120 Layer
122 Layer
130 Inner portion

What is claimed is:

1. An extended release immunomodulatory implant operatively arranged to facilitate bone morphogenesis, comprising:
    an inner portion including one or more interleukins; and,
    a phagocytosable outer portion completely surrounding the inner portion, the outer portion including an antigen operatively arranged to activate an innate immune system;
    wherein the antigen is present in the outer portion prior to implantation.

2. The implant as recited in claim 1, wherein the implant comprises at least one of inert beta-tricalcium phosphate, calcium carbonate, silicon, polylactic-co-glycolic acid, and hydroxyapatite.

3. The implant as recited in claim 1, wherein the inner portion comprises at least one of interleukin 4, interleukin 10, and interleukin 13.

4. The implant as recited in claim 1, wherein the antigen comprises at least one of lipopolysaccharide and lipoteichoic acid.

5. The implant as recited in claim 4, wherein the antigen consists of a mixture of:
    50% by weight lipopolysaccharide; and,
    50% by weight lipoteichoic acid.

6. The implant as recited in claim 4, wherein the antigen consists of 100% by weight lipopolysaccharide.

7. The implant as recited in claim 4, wherein the antigen consists of 100% by weight lipoteichoic acid.

8. The implant as recited in claim 4, wherein the lipopolysaccharide is derived from *Escherichia coli*.

9. The implant as recited in claim 4, wherein the lipoteichoic acid is derived from *Staphylococcus aureus*.

10. The implant as recited in claim 1, wherein the inner portion comprises a first density and the outer portion comprises a second density, the first density being greater than the second density.

11. The implant as recited in claim 1, wherein the inner portion comprises a first porosity and the outer portion comprises a second porosity, the second porosity being greater than the first porosity.

12. The implant as recited in claim 11, wherein the first porosity and the second porosity are connected by one or more channels.

13. The implant as recited in claim 1, wherein the inner portion comprises at least one of inert beta-tricalcium phosphate, calcium carbonate, silicon, polylactic-co-glycolic acid, and hydroxyapatite, impregnated with the one or more interleukins.

14. The implant as recited in claim 1, wherein the outer portion comprises at least one of inert beta-tricalcium phosphate, calcium carbonate, silicon, polylactic-co-glycolic acid, and hydroxyapatite, impregnated with the antigen.

15. The implant as recited in claim 1, wherein the outer portion consists of the antigen.

16. The implant as recited in claim 1, wherein the inner portion comprises:
    an innermost portion including interleukin 10 and interleukin 13; and,
    an inner layer including interleukin 4.

17. The implant as recited in claim 1, wherein:
    the inner portion comprises hydroxyapatite; and, the outer portion comprises:
- an inner layer including beta-tricalcium phosphate including one or more interleukins; and,
- an outer layer including at least one of lipopolysaccharide, lipoteichoic acid, and interferon gamma.

18. The implant as recited in claim 1, wherein the implant comprises at least one of allograft bone, autograft bone, xenograft bone, a titanium implant, a polyether ether ketone (PEEK) implant, and synthetic bone void filler.

19. An extended release immunomodulatory implant operatively arranged to facilitate bone morphogenesis, comprising:
- a singular inner portion including one or more interleukins; and,
- a phagocytosable outer portion completely surrounding the inner portion, the outer portion including an antigen operatively arranged to activate an innate immune system;
- wherein the antigen is present in the outer portion prior to implantation.

* * * * *